United States Patent [19]

Chan et al.

[11] Patent Number: 5,574,066
[45] Date of Patent: Nov. 12, 1996

[54] INTRAOCULAR PRESSURE REDUCING 15-ACYL PROSTAGLANDINS

[75] Inventors: Ming Fai Chan, San Diego; David F. Woodward, El Toro, both of Calif.; Charles Gluchowski, Wayne, N.J.

[73] Assignee: Allergan, Waco, Tex.

[21] Appl. No.: 531,488

[22] Filed: Sep. 21, 1995

Related U.S. Application Data

[63] Continuation of Ser. No. 175,476, Dec. 12, 1993, abandoned, which is a continuation of Ser. No. 967,586, Oct. 28, 1992, abandoned.

[51] Int. Cl.⁶ .................................................. A61K 31/557
[52] U.S. Cl. .................................. 514/548; 514/530
[58] Field of Search ............................................. 514/548

[56] References Cited

U.S. PATENT DOCUMENTS

| | | | |
|---|---|---|---|
| 4,599,353 | 7/1980 | Bito | 560/231 |
| 4,822,819 | 4/1989 | Desantis | 560/231 |

FOREIGN PATENT DOCUMENTS

| | | |
|---|---|---|
| 286903 | 10/1988 | European Pat. Off. . |
| 6448 | 9/1988 | WIPO . |

Primary Examiner—Robert Gerstl
Attorney, Agent, or Firm—Robert J. Baran; Martin A. Voet; Howard R. Lambert

[57] ABSTRACT

A method, compositions and compounds for lowering intraocular pressure involving 15-acyl prostaglandins.

6 Claims, No Drawings

INTRAOCULAR PRESSURE REDUCING 15-ACYL PROSTAGLANDINS

This application is a continuation of application(s) Ser. No. 08/175,476 filed on Dec. 29,1993, now abandoned, which is a continuation of application(s) Ser. No. 07/967,586 filed on Oct. 28, 1992, now abandoned.

BACKGROUND OF THE INVENTION

The present invention relates to a means for reducing or maintaining intraocular pressure. More particularly it relates to a method and composition for reducing or maintaining intraocular pressure involving the administration of a composition containing a 15-acyl prostaglandin in an ophthalmically acceptable carrier.

The method and compositions of the present invention are particularly useful for the management of glaucoma, a disease of the eye characterized by increased intraocular pressure. On the basis of its etiology glaucoma has been classified as primary or secondary. For example, primary glaucoma in adults, congenital glaucoma, may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular tension is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together glaucoma occurs in about 2% of all persons over the age of 40 and may be asymptomatic for years before progressing to rapid loss of vision. In cases where surgery is not indicated, topical B-adrenoceptor antagonists have traditionally been the drugs of choice for treating glaucoma.

Certain eicosanoids and C-1 esters of certain prostaglandins, have been reported to possess ocular hypotensive activity. However, prostaglandin ocular hypotensives generally suffer from the disadvantage of inducing conjunctival hyperemia of varying severity and duration, smarting, and foreign body sensation, as well as presenting solubility problems in certain ophthalmically advantageous carriers.

This invention relates to derivatives of the known prostaglandins formulated in a pharmaceutically acceptable vehicle, and ophthalmic use of these prostaglandins. The present invention has numerous advantages over the prior art, including increasing duration of action or reduction of the aforementioned undesirable side effects, along with being easily solubilized in certain ophthalmically advantageous carriers.

SUMMARY OF THE INVENTION

In accordance with one aspect of the present invention, there is provided compounds and a method of treating ocular hypertension which comprises applying to the eye an amount sufficient to treat ocular hypertension a compounds of following formula.

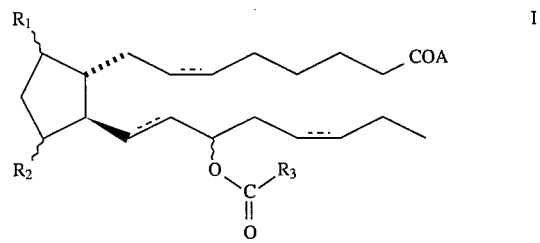

In formula I, the dashed bond represents a single or double bond which can be in the cis or trans configuration; A is —OH, or a pharmaceutically acceptable salt thereof or —OR$_5$; R$_1$/R$_2$ is —OH/—OH, =O/—OH, or —OH/=O; R$_3$ is an acyclic hydrocarbon, saturated or unsaturated, having from 1 to 20 carbon atoms, or R$_3$ is —(CH$_2$)$_n$R$_4$ where n is 0–10 and R$_4$ is an aliphatic ring of from 3 to 7 carbon atoms or an aromatic or heteroaromatic ring, preferably of 5 or 6 carbon atoms; and R$_5$ is an aliphatic radical of from 1 to 10 carbon atoms.

Certain of these 15-acyl prostaglandins are novel chemical entities.

In accordance with another aspect of the present invention, there is provided an ophthalmically acceptable composition for reducing ocular hypertension which comprises at least one 15-acyl prostaglandin described above, present in an ophthalmically acceptable excipient for topical application to the surface of the eye. Such an excipient is one which does not have a deleterious or untoward effect on the eye when used in normal treatment regimens.

Further features and advantages of the present invention will become apparent from the detailed description of preferred embodiments which follows, taken together with the examples and claims appended hereto.

DETAILED DESCRIPTION OF PREFERRED EMBODIMENTS

It has been discovered that certain prostaglandins lower intraocular pressure in man and other mammals when applied topically to the eye. Although the precise mechanism is not yet known, prostaglandins appear to increase aqueous humor outflow to restore a normotensive or hypotensive state. However, topical application of prostaglandins generally causes side effects such as conjunctival hyperemia, smarting and foreign body sensations which range in degree from undesirable to unacceptable, depending upon the particular patient and dosage necessary to produce a sufficient pressure regulating effect.

In accordance with one aspect of the present invention, there has been provided a method for treating ocular hypertension which comprises administering to the eye a compound of formula I. It has further been discovered that these esters are more effective than PGF$_{2\alpha}$ both in terms of degree and duration of activity. In addition, animals treated with formulations comprising these esters experience reduced adverse side effects, notably ocular surface hyperemia.

In the foregoing illustration, as well as those provided hereinafter, wavy line attachments indicate either the alpha (α) or beta (β) configuration. The dotted lines on bonds between carbons 5 and 6 (C-5), between carbons 13 and 14 (C-13), and between carbons 17 and 18 (C-17) indicate a single or double bond which can be in the cis or trans configuration. If two solid lines are used at C-5, C-13, or C-17, that indicates a specific configuration for that double bond. Hatched lines used at positions C-9, C-11 and C-15 indicate the α configuration. If one were to draw the β configuration, a solid triangular line would be used at either of these three positions.

The naturally occurring stereochemistry of $PGF_{2\alpha}$ includes the C-9, C-11 and C-15 hydroxyl groups in the α configuration. In the compositions of the present invention, however, esters of prostaglandins having the C-9 or C-11 or C-15 hydroxyl group in the β configuration are also contemplated. In addition to configurational variations, the substituent group at each of the 9 and 11 positions may be varied. Designating the C-9 substituent as $R_1$, and the $C_{11}$ substituent as $R_2$, 15-acyl prostaglandins for use in the method of the present invention may be substituted such that $R_1$ and $R_2$ taken together in that order are —OH/—OH, =O/—OH, or —OH/=O.

The 15-acyl prostaglandins suitable for use in this invention can comprise any of a variety of acyl substituents at the 15 position. As per formulas I, $R_3$ can be an aliphatic acyclic hydrocarbon having from one to twenty carbon atoms, inclusive. Preferably $R_3$ has from one to ten carbon atoms. More preferably $R_3$ is methyl, ethyl, propyl, butyl, pentyl, or an isomeric form thereof. The preferred isomeric forms are the isopropyl, n-butyl, isobutyl or t-butyl isomers.

Alternatively $R_3$ can comprise a cyclic component. In particular, $R_3$ can be $(CH_2)_nR_4$ where n is 0–10 and $R_4$ is a saturated or unsaturated ring, preferably a saturated ring having from three to seven carbon atoms, inclusive, or an aromatic or heteroaromatic ring of 5 to 7 carbon atoms, and having oxygen, nitrogen or sulfur in the case of a heteroaromatic ring. Preferably n is 0–4.

In all formulations provided herein broken line attachments to the cyclopentane ring indicate substituents in the α configuration. Thickened solid line attachments to the cyclopentane ring indicate substituents in the β configuration. For instance, $9_\beta$-PGF compounds have the same structure as the above $PGF_\alpha$ compounds, except that the hydroxyl at the C-9 position is in the β configuration. Also, the broken line attachment of the hydroxyl group to the C-15 carbon atom signifies the α configuration; therefore, compounds with the epi configuration for the hydroxyl group at C-15 are designated by using 15β and if there is no indication of the β configuration, the configuration is assumed to be α.

The preferred compounds of this invention are those which have the following structures.

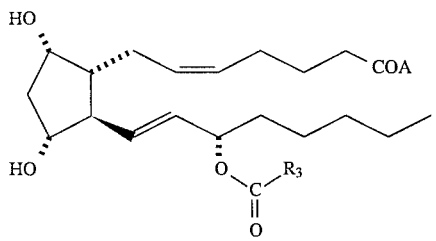

-continued

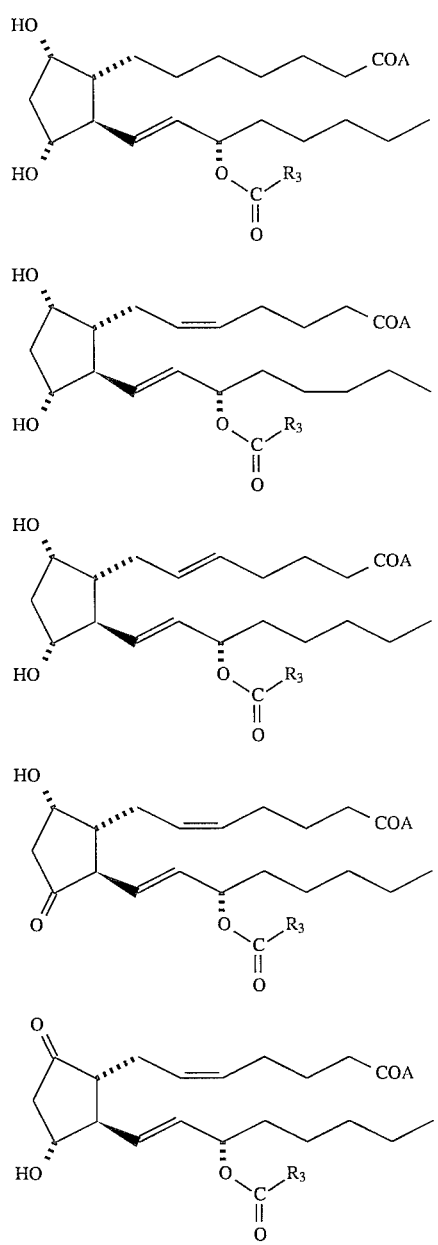

Within this preferred group, the most preferred compounds are those where $R_3$ is —$CH(CH_3)_2$—$(CH_2)_3CH_3$, —$CH_2CH(CH_3)_2$ or —$C(CH_3)_3$.

Where A is —OH the acid can be converted to a salt $O^-X^+$ where $X_+$ is the anion component of any of a variety of pharmaceutically acceptable salts. A pharmaceutically acceptable salt may be prepared for any compound in this disclosure having a functionality capable of forming such salt, in particular, the carboxylic acid group at $C_1$ of the prostaglandins disclosed herein. A pharmaceutically acceptable salt is any salt which retains the activity of the parent compound and does not impart any deleterious or undesirable effect on the subject to which it is administered and in the context in which it is administered.

A pharmaceutically acceptable salt of an acid may be derived from an organic or inorganic base. Such salt may be a mono- or polyvalent ion. Of particular interest are the inorganic ions, sodium, potassium, calcium, magnesium, and zinc. Organic ammonium salts may be made with amines, such as mono-, di-, and trialkyl amines or ethanolamines. Salts may also be formed with caffeine, tromethamine and similar molecules.

In another aspect, this invention relates to a composition which can be applied topically to the eye to lower intraocular pressure. This composition comprises one or more of the foregoing 15-acyl prostaglandins therein. The composition may comprise any of a variety of ophthalmically acceptable carriers as will be known to those skilled in the art of ocular drug delivery. A preferred method of application would be topically, in a pharmaceutically acceptable topical formulation. Such a carrier may be comprised of a saline and/or detergent, containing pharmaceutically required or advantageous adjuvants, along with an effective dose of the intraocular pressure reducing drug.

In accordance with a preferred embodiment of the present invention, the carrier comprises a solution having polysorbate 80–10 mM TRIS in the range of from about 0.05–1.0% by weight, and preferably about 0.1%, which is particularly suited for administration in the form of a liquid eye drop. This carrier may additionally comprise pharmaceutically advantageous adjuvants such as a preservative, antibiotic/antimycotic agents, pH buffers or osmotic balancers. In a preferred embodiment of the present invention, the intraocular pressure-reducing agent comprises a derivative of $PGF_{2\alpha}$, preferably one or a combination of the 15-isobutyryl, 15-valeryl, 15-isovaleryl or 15-pivaloyl $PGF_{2\alpha}$ derivatives.

The optimal concentration of the prostaglandin derivative is a function of a variety of factors, such as desired frequency of application and duration of effect, level of adverse side effects and considerations implicated by the chemical nature of the carrier. In general, however, concentrations are contemplated within the range of from about 0.0001% to 1%, preferably from 0.001% to 0.1% by weight in relation to the pharmaceutically acceptable carrier.

The esterification reactions for producing these 15-acyl compounds are illustrated in the Examples or are known to those skilled in the synthetic organic chemical arts.

The invention can be more fully understood by the following examples. All temperatures are in degrees centigrade.

EXAMPLE 1

Preparation of 15-Acetyl $PGF_{2\alpha}$ $PGF_{2\alpha}$ (50.1 mg, 0.14 mmol) (Toray), n-butane boronic acid (28.8 mg, 0.282 mmol) and pyridine (2.0 ml) were combined. The reaction was stirred at 25° for 1.25 hours. Acetic anhydride (2 ml) was then added and the mixture was stirred continuously at 25° for 26 hours. The reaction mixture was cooled to 0° and quenched with water (3 ml). The reaction mixture was then concentrated in vacuo at 30° to yield a yellow oil. The oil was redissolved in approximately 10 ml of ethyl acetate and washed with a 0.2 M citrate buffer. The resulting aqueous layer was saturated with NaCl and extracted with ethyl acetate. The combined organic phases were dried over magnesium sulfate, concentrated and chromatographed (HPLC, Whatman ODS-2 M-9, 60/40 $CH_3CN/H_2O$ elution) to yield the title compound as a colorless oil.

$^1H$ NMR ppm ($CDCl_3$): δ 5.30–5.65(m), 5.15(q), 4.45(br), 4.20(br,s), 4.05(br,s), 1.45–2.30(m), 2.05(s), 1.30(br), 0.95(t).

$^C$NMR ppm ($CDCl_3$): δ 177.8, 170.8, 134.6, 130.1, 129.6, 129.1, 78.1, 74.9, 73.2, 55.8, 50.6, 42.7, 34.5, 33.0, 31.5, 26.4, 25.7, 24.9, 24.5, 22.5, 21.4, 14.0.

EXAMPLE 2

Preparation of 15-Isobutyryl $PGF_{2\alpha}$ $PGF_{2\alpha}$ (60.2 mg, 0.17 mmol) (Toray), n-butane boronic acid (26.3 mg, 0.25 mmol) and methylene chloride (0.5 ml) were heated at reflux for 20 minutes before removal of the methylene chloride under a stream of dry nitrogen. The residue was dried in vacuo for 1.5 hours to remove water. This gave the intermediate 9,11boronate derivative.

The resulting colorless boronate derivative was redissolved in methylene chloride (0.5 ml), cooled to 0° and treated with triethylamine (50.5 mg, 0.6 mmol), 4-dimethylaminopyridine (10 mg) and isobutyric anhydride (85.4 mg, 0.54 mmol). The reaction mixture was warmed to 25° and stirred for 22 hours before being concentrated in vacuo redissolved in ethyl acetate and washed with a 0.2 M citrate buffer. The ethyl acetate layer was dried over $MgSO_4$, concentrated in vacuo and chromatographed on HPLC to yield the title compound as a colorless oil.

$^1$HNMR ppm ($CDCl_3$): δ5.10–5.25(m), 5.15(q), 4.21(t), 3.99(t), 3.40–5.00(br), 2.50(m), 1.00–2.40(m), 0.95(t).

$^{13}$CNMR ppm($CDCl_3$): δ 177.9, 176.8, 134.3, 130.3, 129.6, 129.1, 78.2, 74.3, 73.3, 55.8, 50.6, 42.7, 34.5, 34.2, 33.1, 31.5, 26.4, 25.7, 24.8, 24.5, 22.5, 19.0, 18.9, 13.9.

Proceeding in a similar manner, but substituting for the isobutyric anhydride either valeryl chloride or isovaleryl chloride there was made the following two compounds:

15-valeryl $PGF_{2\alpha}$ -$^1$HNMR ($CDCl_3$): 8 5.18–5.58(m), 5.15(q), 4.18(m), 3.98(m), 1.18–2.44(m), 0.91(t).

$^{13}$CNMR($CDCl_3$): δ 177.9, 173.6, 134.5, 130.3, 129.7, 129.2, 78.2, 74.6, 73.3, 55.9, 50.7, 42.7, 34.6, 34.5, 33.0, 31.5, 27.1,26.4, 25.7, 24.9.24.5, 22.6, 22.3, 14.0, 13.8.

15-isovaleryl $PGF_{2\alpha}$-$^1$HNMR ($CDCl_3$): δ 8 5.25–5.60(m), 5.15(m), 4.25(m), 4.18(m), 4.11(m), 3.98(m), 1.05(m)-2.45(m), 0.95(δ), 0.91(t).

$^{13}$CNMR ($CDCl_3$): δ 8 177.9, 172.5, 134.5, 130.2, 129.6, 129.1, 78.2, 74.5, 73.3, 55.8, 50.6, 43.8, 42.7, 4.5, 33.0, 31.5, 26.4, 25.8, 24.9, 24.5, 22.5, 22.4, 13.9.

EXAMPLE 3

Preparation of 15-Pivaloyl $PGF_{2\alpha}$ $PGF_{2\alpha}$ (40.4 mg, 0.114 mmol) was suspended in methylene chloride (1 ml) and cooled to 0° with an ice bath. A solution of diazomethane in ether was added dropwise to the above suspension until a yellow color persisted. The solution was warmed to 25° for 30 minutes before concentration in vacuo to yield the $PGF_{2\alpha}$ methyl ester as an oil. The crude ester was combined with n-butyl boronic acid (14 mg, 0.137 mmol) in methylene chloride (0.25 ml) and heated at reflux for 30 minutes. The reaction mixture was concentrated in vacuo and the residue dissolved in dry benzene. The benzene was evaporated under reduced pressure. The process was repeated twice to remove traces of water present from the reaction.

The crude $PGF_{2\alpha}$ 9,11-n-butyl boronate methyl ester thus prepared was dissolved in 0.2 ml of dry pyridine and treated with trimethylacetylchloride (42 μl, 0.34 mmol) and 4-dimethylamino pyridine (about 1 mg). The reaction mixture was stirred at 25° for 14 hours before being concentrated in vacuo. The residue was dissolved in ethyl acetate (10 ml) and washed with 10% aqueous citric acid (7 ml). The aqueous phase was extracted with ethyl acetate (3×7 ml) and the combined organic extract was washed with brine (7 ml), dried over magnesium sulfate and concentrated in vacuo. The residue was dissolved in methanol (3ml) and stirred at 25° for 2 hours. The solvent was removed in vacuo and replaced with fresh methanol. This process was repeated once more. After removal of solvent, the residue was chromatographed (silica gel; 50–60% ethyl acetate/hexanes) to yield the 15-pivaloyl $PGF_{2\alpha}$ methyl ester as an oil.

15-pivaloyl $PGF_{2\alpha}$ methyl ester, (29.4 mg, 0.065 mmol) was dissolved in 0.33 ml of tetrahydrofuran and aqueous 0.5 M lithium hydroxide solution (0.16 ml) was added dropwise at 0°. The two-phase mixture was stirred vigorously at 0° for 7 hours and at 25° for 1 hour. The mixture was cooled to 0° and acidified with 10% citric acid (7 ml). The reaction mixture was extracted with ethyl acetate (3×10 ml) and the combined organic extract was washed with brine (7 ml), dried over magnesium sulfate and concentrated in vacuo to yield the crude product. Flash chromatography on silica gel (6:4 ethyl acetate/hexanes with 0.5% acetic acid) yielded a colorless oil which was rechromatographed (6:4 ethyl acetate/hexanes) to yield purified 15-pivaloyl $PGF_{2\alpha}$.

$^1HNMR$ (300 MHz, $CDCl_3$): δ 5.3–5.6 (m, 4H);5.17 (q, J=7 Hz, 1H); 4.17 (br s, 1H); 2.34 (t, J=7 Hz, 2H); 2.0–2.4 (m, 7H); 1.2–1.9 (m-11H); 1.18 (s, 9H); 0.86 (distorted t, J =7Hz, 2H);

$^{13}CNMR$ (75 MHz, $CDCl_3$): δ 5178.9, 178.3, 134.2, 130.5, 129.3, 78.2, 74.2, 73.3, 55.7, 50.5, 42.5, 38.7, 34.4, 32.9, 1.3, 26.9, 26.2, 26.2, 25.5, 24.6, 24.3, 22.3, 13.7.

EXAMPLE 4

Preparation of 15-acyl $PGE_2$

Preparation of 15-acyl $PGE_2$ derivatives may be effected by the procedure described in Bundy, G. L., *J. Am. Chem. Soc.*, 1972, 94, 2123.

$PGA_2$(0.34 gm 1 mmol) is dissolved in pyridine (1 ml) and treated with acetic anhydride (1 ml). After 24 hours at room temperature, the reaction mixture is quenched with water (0.5 ml), concentrated in vacuo and the residue chromatographed to yield 15acetyl $PGA_2$. The 15-acetyl $PGA_2$(0.282 g, 0.75 mmol) is then treated with 30% aqueous hydrogen peroxide (2 ml) and 1N aqueous sodium hydroxide (2 ml) in tetrahydrofuran (2 ml) for 8 hours to obtain 10,11-epoxy 15-acetyl $PGA_2$ after concentration in vacuo and chromatographic purification. Reduction of the 10,11-epoxy 15-acetyl $PGA_2$ (0.195 g, 0.5 mmol) with chromous acetate (0.376 g, 1 mmol) in acetic acid (2 ml) produces 15-acetyl $PGE_2$ along with 11-β-15-acetyl $PGE_2$ after chromatography. When acetic anhydride is replaced with another acid anhydride or acid chloride, the corresponding 15-acyl $PGE_2$ can be obtained.

EXAMPLE 5

Preparation of 15-acyl $PGD_2$ $PGD_2$(1 mmol, 0.35 g) is dissolved in $CH_2Cl_2$ (2ml) and treated with pyridine (3 mmol, 0.24 g) and acetic anhydride (1 mmol, 0.10 g). The reaction mixture is stirred at room temperature for 24 hours before being quenched with water. The organic layer is separated, dried over magnesium sulfate and concentrated to yield a residue which is chromatographed to yield 15-acetyl $PGD_2$. When acetic anhydride is replaced with another acid anhydride or acid chloride, the corresponding 15-acyl $PGD_2$ can be obtained.

In accordance with minor variations on the procedures set forth in Examples 1–5 above, any of the 15-esters contemplated by this invention may be made.

EXAMPLE 6

Intraocular Pressure Reducing Effect in Rabbits

Starting with $PGF_{2\alpha}$, experimental quantities of the 15-acetyl, 15-isobutyryl, 15-valeryl, 15-isovaleryl and 15-pivaloyl esters were prepared in accordance with the procedure of Example 1–6. The resulting 15-acyl $PGF_{2\alpha}$ compounds were added to a polysorbate carrier in amounts to produce a 0.01% and 0.1% solution of each ester. A group of 8 experimental rabbits was treated by administering one drop of each solution to the surface of the eye, and intraocular pressure was measured by applanation pneumatonometry (Model 30 RT manufactured by Digilab) at the time of administration and at intervals of 3, 4, 6, 8 and 10 hours thereafter. The data of Table I were obtained:

TABLE I

DECREASES IN INTRAOCULAR PRESSURE AT PREDETERMINED TIMES (HR) AFTER PROSTAGLANDIN ADMINISTRATION

| PG Dose % | Time (Hours) | | | | | |
|---|---|---|---|---|---|---|
| | 0 | 3 | 4 | 6 | 8 | 10 |
| $PGF_{2\alpha}$ | | | | | | |
| 0.01% | 0 | −2.3* | −1.3 | −0.25 | — | — |
| 0.1% | 0 | −6.1** | −3.9** | −2.2** | −1.1 | |
| 15-Acetyl $PGF_{2\alpha}$ | | | | | | |
| 0.01% | 0 | 1.3 | −0.7 | — | — | — |
| 0.1% | 0 | −3.3** | −3.3** | — | | |
| 15-Valeryl $PGF_{2\alpha}$ | | | | | | |
| 0.01% | 0 | −2.4** | −2.3** | −2.0 | — | — |
| 0.1% | 0 | −0.25 | −5.4** | −7.6** | — | — |
| 15-Isobutyryl $PGF_{2\alpha}$ | | | | | | |
| 0.01% | 0 | −5.0** | −4.4** | −2.0* | — | — |
| 0.1% | 0 | −2.75 | −3.4 | −6.6* | −5.6* | −4.7* |
| 15-Isovaleryl $PGF_{2\alpha}$ | | | | | | |
| 0.01% | 0 | −4.0** | −5.1** | −5.2** | — | — |
| 0.1% | 0 | −1.5 | −5.1** | −7.5** | −5.2** | −3.2** |
| 15-Pivaloyl $PGF_{2\alpha}$ | | | | | | |
| 0.01% | 0 | — | −3.4 | −4.7** | −3.5 | −1.6 |
| 0.1% | 0 | — | −0.25 | −9.3** | −9.7** | −7.4** |

*$p < 0.05$,
**$p < 0.01$,
n = 8

Comparison of the intraocular pressure-reducing effects of the foregoing series of 15-acyl $PGF_{2\alpha}$ esters with the parent compound reveals a marked increase in both the degree and duration of activity. Thus, with the 0.01% and 0.1% doses of the 15-isobutyryl, 15-valeryl, 15-isovaleryl and 15-pivaloyl esters, the magnitude of the decrease in intraocular pressure achieves a level that does not occur for either the 0.01% or 0.1% dose of $PFG_{2\alpha}$. Moreover, the response to these 15-acyl $PGF_{2\alpha}$ a derivatives appears more persistent than those recorded for $PGF_{2\alpha}$. In addition, the 15-acyl derivatives produce less hyperemia that the parent compound.

EXAMPLE 7

Intraocular Pressure

Studies comparing the effects of $PGF_{2\alpha}$-15-pivalate, $PFG_{2\alpha}$, and its 1-isopropyl ester on dog intraocular pressure (IOP) and ocular surface hyperemia were performed using 0.5 to 1 year old Beagle dogs as test animals. Intraocular pressure was measured with a pneumotonometer following standard experimental procedures. Corneal anesthesia for tonometry was provided by one drop of 0.05% proparacaine. Intraocular pressure was recorded immediately before drug administration, and again at predetermined times thereafter. Prostanoid solutions were prepared in a 0.1% polysorbate/ 10mM TRIS formulation which was topically applied to one eye as a control.

For assessment of ocular irritation, prostanoid formulations were prepared and administered in an identical manner to Beagle dogs (0.5–1year old). The eyes of each dog were examined prior to drug administration. Ocular surface hyperemia was assessed by observation at predetermined times after drug administration and is described as either present or absent. The obtained result are shown in the following Table II.

TABLE II

The effects of $PGF_{2\alpha}$ 15-plvalate, $PGF_{2\alpha}$n-1-Isopropyl ester, and $PGF_{2\alpha}$ on dog intracular pressure and ocular surface hyperemia are compared in the following table:

| PROSTAGLANDIN | Dose (%) | 1 HR | 2 HR | 4 HR | 6 HR | 8 HR |
|---|---|---|---|---|---|---|
| | | DOG INTRAOCULAR PRESSURE INTRAOCULAR PRESSURE (mmHg) CHANGES AT PREDETERMINED TIMES (HR) AFTER PROSTAGLANDIN ADMINISTRATION | | | | |
| $PGF_{2\alpha}$ | 0.1% | −2.4 | −1.3 | −4.8** | −4.5** | −5.25* |
| $PGF_{2\alpha}$-1-Isopropyl ester | 0.1% | −3.6 | −2.8** | −6.3* | −9.1** | −10.3* |
| $PGF_{2\alpha}$-15-plvalate | 0.1% | −0.9 | +0.4 | −3.4** | −6.6** | −7.5** |
| | | DOG OCULAR SURFACE HYPEREMIA PERCENT ANIMALS EXHIBITING OCULAR SURFACE HYPEREMIA % HYPEREMIA AT PREDETERMINED TIMES (HR) | | | | |
| $PGF_{2\alpha}$ | 0.1% | 100 | 100 | 100 | — | 75 |
| $PGF_{2\alpha}$-1-Isopropyl ester | 0.1% | 100 | 100 | 75 | — | 75 |
| $PGF_{2\alpha}$-15-plvalate | 0.1% | 0 | 0 | 0 | — | 0 |

*p = 0.05
**p < 0.01
n =0 4–6

The results set forth in Table II clearly demonstrate that although $PGF_{2\alpha}$, $PGF_{2\alpha}$ -1-isopropyl ester and $PGF_{2\alpha}$ -15 pivalate all effectively lowered intraocular pressure, both $PGF_{2\alpha}$ and its isopropyl ester caused persistent ocular surface hyperemia, whereas $PFG_{2\alpha}$ -15-pivalate was almost entirely devoid of this side effect. Thus, the favorable separation between ocular hypotension and ocular surface hyperemia is even more striking in the dog than in lower species.

Although this invention has been described in terms of certain preferred embodiments, other embodiments that are apparent to those of ordinary skill in the art are also within the scope of this invention. Accordingly, the scope of the invention is intended to de defined only by reference to the appended claims.

What is claimed is:

1. A method of treating ocular hypertension which comprises applying to the eye in an ophthalmically acceptable excipient an amount sufficient to treat ocular hypertension of the compound:

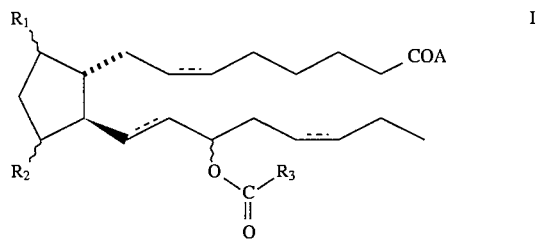

wherein A is —OH or a pharmaceutically acceptable salt thereof; $R_1$ and $R_2$ combined are —OH/—OH; $R_3$ is an acyclic hydrocarbon, saturated or unsaturated, having from 1 to 20 carbon atoms, the C-5 and C-13 bonds are cis and trans respectively and each $R_1$ and $R_2$ and the 15-acyl group are group in the α configuration.

2. The method of claim 1 wherein $R_3$ is ethyl, propyl, butyl, or pentyl or an isomeric form thereof.

3. The method of claim 2 where $R_3$ is —CH(CH$_3$)$_2$, —(CH$_2$)$_3$CH$_3$, —CH$_2$CH(CH$_3$)$_2$ or —C(CH$_3$)$_3$.

4. An ophthalmically acceptable composition for reducing ocular hypertension which comprises an ophthalmically acceptable excipient and at least one compound of the formula:

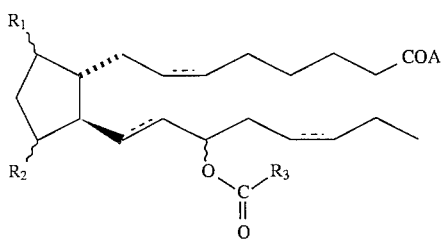

wherein A is —OH or a pharmaceutically acceptable salt thereof; $R_1$ and $R_2$ combined are —OH/—OH, $R_3$ is an acyclic hydrocarbon, saturated or unsaturated, having from 1 to 20 carbon atoms the C-5 and C-13 bonds are cis and trans respectively, each $R_1$ and $R_2$ group and the 15-acyl group are in the α configuration.

5. The composition of claim 4 where $R_3$ is ethyl, propyl, butyl or pentyl, or an isomeric form thereof.

6. The composition of claim 5 wherein the R3 group is —$CH(CH_3)_2$, —$(CH_2)_3CH_3$, $CH_2CH(CH_3)_2$ or —$C(CH_3)_3$.

* * * * *

UNITED STATES PATENT AND TRADEMARK OFFICE
CERTIFICATE OF CORRECTION

PATENT NO. : 5,574,066                                    Page 1 of 3
DATED     : November 12, 1996
INVENTOR(S): Chan et al It is certified that error appears in the above-indentified patent and that said Letters Patent is hereby corrected as shown below:

Column 1, line 50; after "together" insert -- , --

Column 3, line 13; delete "8" and insert in place thereof -- β --

Column 4, line 15; delete first formula and insert in place thereof

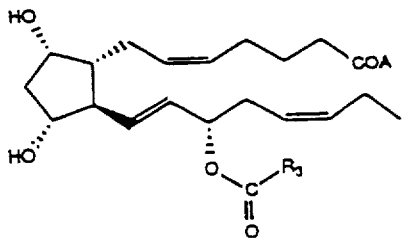

-- --

Column 4, line 54; delete "$X_+$" and insert in place thereof --$X^+$--

Column 5, line 56; delete "in vacuo" and insert in place thereof --<u>in vacuo</u>--

Column 5, line 62; after "concentrated" insert --<u>in vacuo</u>--

Column 6, line 1; delete "CNMR" and insert in place thereof --$^{13}$CNMR--

Column 6, line 8; delete "n-butane" and insert in place thereof --<u>n</u>-butane--

Column 6, line 13; delete "in vacuo" and insert in place thereof --<u>in vacuo</u>--

Column 6, line 20; delete "in vacuo" and insert in place thereof --<u>in vacuo</u>,--

Column 6, line 24; delete "in vacuo" and insert in place thereof --<u>in vacuo</u>--

Column 6, line 33; delete "8" and insert in place thereof --δ--

Column 6, line 39; delete "8"

Column 6, line 42; delete "8"

Column 6, lines 54-55; delete "in vacuo" and insert in place thereof --<u>in vacuo</u>--

Column 6, line 56; delete "n-butyl" and insert in place thereof --<u>n</u>-butyl--

UNITED STATES PATENT AND TRADEMARK OFFICE
CERTIFICATE OF CORRECTION

PATENT NO. : 5,574,066
DATED : November 12, 1996
INVENTOR(S) : Chan et al

Page 2 of 3

It is certified that error appears in the above-indentified patent and that said Letters Patent is hereby corrected as shown below:

Column 6, lines 58-59; delete "in vacuo" and insert in place thereof --in vacuo--

Column 6, line 63; delete "n-butyl" and insert in place thereof --n-butyl--

Column 6, line 67; delete "in vacuo" and insert in place thereof --in vacuo--

Column 7, line 5; delete "in vacuo" and insert in place thereof --in vacuo--

Column 7, line 7; delete "in vacuo" and insert in place thereof --in vacuo--

Column 7, line 20; delete "in vacuo" and insert in place thereof --in vacuo--

Column 7, line 29; delete "5178.9" and insert in place thereof --178.9--

Column 7, line 30; delete "29.8" and insert in place thereof --129.8--

Column 7, line 31; delete "1.3" and insert in place thereof --31.3--

Column 7, line 43; delete "in vacuo" and insert in place thereof --in vacuo--

Column 7, line 45; delete "15acetyl" and insert in place thereof --15-acetyl--

Column 7, line 48; delete "in vacuo" and insert in place thereof --in vacuo--

Column 7, line 62; delete "With" and insert in place thereof --with--

Column 7, line 66; after "concentrated" insert --in vacuo--

Column 8, line 65; delete "a"

UNITED STATES PATENT AND TRADEMARK OFFICE
CERTIFICATE OF CORRECTION

PATENT NO.  : 5,574,066
DATED       : November 12, 1996
INVENTOR(S) : Chan et al It is certified that error appears in the above-indentified patent and that said Letters Patent is hereby corrected as shown below:

Column 9, line 2 of Table II; delete "$PGF_2n-1$" and insert in place thereof --$PGF_{2\alpha}-1$--

Signed and Sealed this

Eighteenth Day of March, 1997

BRUCE LEHMAN

*Attest:*

*Attesting Officer*    *Commissioner of Patents and Trademarks*